Figure 1:
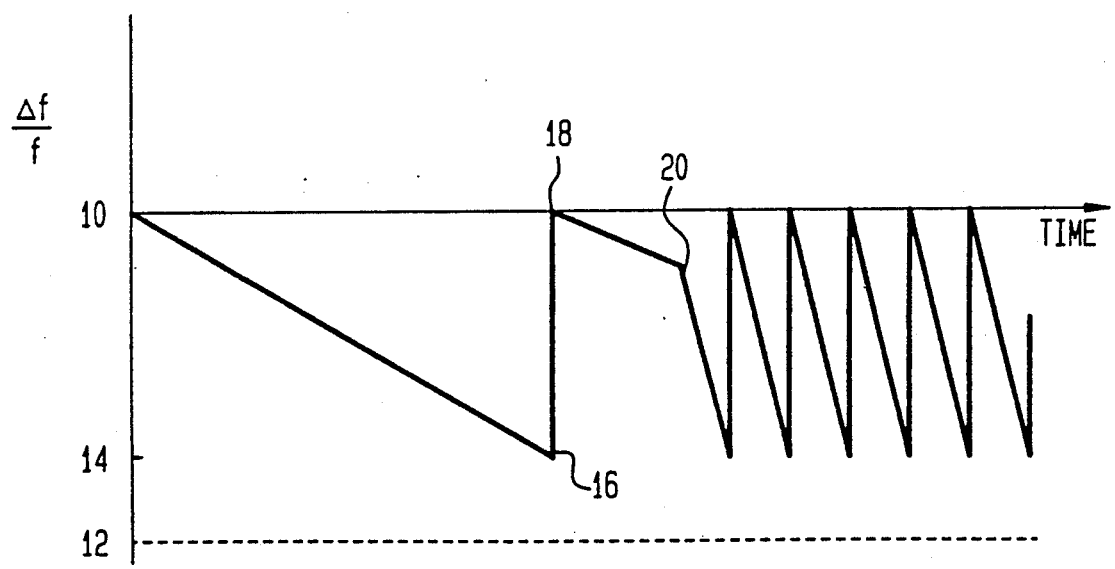

United States Patent [19]

Vig

[11] Patent Number: 5,042,288

[45] Date of Patent: Aug. 27, 1991

[54] METHOD OF SENSING CONTAMINATION IN THE ATMOSPHERE

[75] Inventor: John R. Vig, Colts Neck, N.J.

[73] Assignee: The United States of America as represented by the Secretary of the Army, Washington, D.C.

[21] Appl. No.: 528,525

[22] Filed: May 25, 1990

[51] Int. Cl.$^5$ ............................................. G01N 31/00
[52] U.S. Cl. ............... 73/24.001; 73/24.003; 422/88; 422/98
[58] Field of Search ................. 73/24.01, 24.03; 422/98, 24

[56] References Cited

U.S. PATENT DOCUMENTS

| | | | |
|---|---|---|---|
| 3,897,992 | 4/1975 | Bartera | 73/30 |
| 3,981,687 | 9/1976 | Vig | 29/25.35 |
| 4,760,351 | 4/1988 | Newell et al. | 331/48 |

Primary Examiner—Hezron E. Williams
Assistant Examiner—William Francos
Attorney, Agent, or Firm—Michael Zelenka; Roy E. Gordon

[57] ABSTRACT

Contamination in the atmosphere is sensed and identified using unsealed dual mode resonators and a means to clean the resonators in an ongoing method to measure contamination induced frequency change with time, while compensating for temperatures induced frequency shifts.

14 Claims, 1 Drawing Sheet

METHOD OF SENSING CONTAMINATION IN THE ATMOSPHERE

The invention described herein may be manufactured, used, and licensed by or for the Government for governmental purposes without the payment to me of any royalty thereon.

This invention relates to a method of sensing contamination in the atmosphere, and in particular to such a method that is continuous and realtime and in which the frequency change of an unsealed dual mode quartz crystal resonator is used to measure contamination induced frequency change with time.

BACKGROUND OF THE INVENTION

Several methods of detecting airborne contaminants are available, including gas chromatography, Fourier transform infrared spectroscopy, ionization techniques, electrochemical techniques, and adsorption by means of a charcoal canister. These methods require either very expensive equipment, or for the less expensive methods, results are either inaccurate or not available realtime. For example, in the past, charcoal detectors have been used to detect organic airborne contaminants in the atmosphere such as air pollutants, toxic gases, outgassing products, etc. In that method, the charcoal materials absorbed the contaminant, and the charcoal was later analyzed. The difficulty with the charcoal detection method was that the results were obtained after the fact. In other words, the results of contamination detection were delayed.

Recently, the use of quartz crystal sensors has been suggested as a means of sensing contamination in the atmosphere but the accuracy of sensing has been limited by uncertainties due to not knowing the resonator's temperature. For example, the frequency of the resonator may change by about 1 part per million per degree C. This means that if the output frequency of a sensor changes by 0.1 part per million, it could be due either to contamination or to a temperature change of 0.1 degree C.

SUMMARY OF THE INVENTION

The general object of this invention is to provide a continuous and realtime method of sensing contamination in the atmosphere. A more particular object of the invention is to provide such a method in which the frequency change of an unsealed dual mode quartz crystal resonator is used to measure contamination induced frequency change as a function of time. A still further object of the invention is to provide such a method in which temperature is eliminated as an interfering factor in the measurement of contamination induced frequency change.

It has now been found that the aforementioned objects can be attained and an ongoing method of sensing contamination in the atmosphere provided by using an unsealed dual mode quartz crystal resonator to measure contamination induced frequency change as a function of time. More particularly, the invention includes the steps of (A) cleaning the electrodes of the resonator, (B) allowing contamination from the atmosphere to be adsorbed onto the resonator and simultaneously measuring the resultant decrease in frequency with time until nearly a monolayer of contamination has been adsorbed onto the resonator while compensating for temperature induced frequency shifts, and (C) repeating steps (A) and (B).

This invention makes use of the fact that a very precise means of a resonator to sense its own temperature is provided by S. Schodowski in U.S. Pat. No. 4,872,765, issued Oct. 10, 1989 for "Dual Mode Thermometric Sensing Device." In other words, the self temperature sensing method of Schodowski is used by applicant herein to eliminate temperature as an interfering factor in the measurement of contamination induced frequency change. Alternatively, the b-mode of a doubly rotated resonator can be used for resonator self-temperature sensing.

In the instant invention the frequency change with tim of an unsealed dual mode quartz crystal resonator is used to sense the adsorption of contamination onto the resonator. If initially, the electrodes are cleaned, then the rate of change of frequency with time is directly proportional to the rate of arrival of contaminant molecules. That is, the rate of change of frequency is directly proportional to the contaminant concentration near the resonator. Once the electrodes become contaminated, the rate of change of frequency is no longer a good measure of contaminant concentration near the resonator. To insure that the sensor remains a good detector of contamination, indefinitely, applicant includes a cleaning of the resonator as for example a UV-ozone cleaning to periodically remove contaminants from the electrode surface.

DESCRIPTION OF THE DRAWING AND THE PREFERRED EMBODIMENT

To carry out the method of the invention, there is assembled an unsealed 10 megahertz third overtone SC-cut resonator in a dual mode oscillator. Two small UV-ozone cleaners are placed within 2 centimeters of the resonator, and a frequency counter connected to the output terminals of the oscillator.

The UV-ozone cleaners are arranged on either side of the resonator such that one cleaner cleans one side of the resonator and the other UV-ozone cleaner cleans the other side. The UV-ozone cleaners can be inexpensive short-wave length UV penlights, for example. The dual mode oscillator excites the resonator both at the 10 MHz frequency and at the fundamental mode frequency at about 3.3 MHz. The outputs of the dual mode oscillator are used for self temperature sensing as is well known in the art, and for compensation of the sensor's frequency change for temperature effects. One may use either the 10 MHz frequency or the 3.3 MHz frequency for sensing the contamination. Since the adsorption of contamination will cause nearly identical normalized frequency changes in the two modes, the self temperature sensing method's accuracy will not be degraded significantly by the adsorption and desorption of contamination.

The electronics needed to sense the frequency change due to contamination can be, for example, appropriately modified versions of the microcomputer compensated crystal oscillators (MCXO) that are described in "Microcomputer-compensated Crystal Oscillator for Low Power Clocks", by S. S. Schodowski, et al., in the Proceedings of the Twenty First Annual Precise Time and Time Interval (PTTI) Applications and Planning Meeting, 1989.

To see that the sensitivity of the subject contamination detector is extremely high, consider that the mass of a 10 MHz fundamental-mode SC-cut resonator is 0.045 g/cm$^2$. Assuming an airborne contaminant arrival rate of 10 pg/cm$^2$ sec, which is a typical rate found in a clean room under normal conditions, the normalized frequency change is given by $\Delta f/f = \Delta m/m = 2 \times 10^{-10}$/second, or $1.3 \times 10^{-8}$/minute. Such a rate of change in frequency is readily measurable by means of art established methods. The thermometry sensitivities of the dual-mode self temperature sensing methods are typically about 100 ppm/° C., so that measuring the thermometry mode with a resolution of $1 \times 10^{-7}$ corresponds to knowing the temperature to $10^{-3}$° C. In Schodowski's method, for example, if the turnover temperature of the contamination sensing mode is set to be at ambient temperature, then the frequency changes due to changes or fluctuations in the ambient temperature will be about 0.1 to 1 ppm/°C. Therefore a temperature uncertainty of $10^{-3}$° C. corresponds to a frequency uncertainty of about $1 \times 10^{-10}$ to $1 \times 10^{-9}$, which corresponds to the amount of contamination adsorbed in 0.5 to 5 seconds. Hysteresis will degrade the resolution somewhat, however, if the frequency is monitored continuously (e.g., with a 10 second averaging time), then much of the noise due to temperature fluctuations, and the corresponding hysteresis, can be filtered out.

The resonator electrodes determine the selectivity of the subject contamination detector. For example, when one uses gold electrodes, the detector measures contamination nonselectively since gold adsorbs most organic and many other types of gases. The same is true when the electrodes are made of a thin film of carbon. One can make a more specific detector by coating the electrodes with selective adsorbers (e.g , enzymes and lipids can be selective adsorbers, although the UV-resistance of such adsorbers would need to be also considered). Carbon films would have a higher capacity for adsorbing organic contamination than gold. This would require less frequent need to clean the contaminants from the electrodes, however, the UV-ozone cleaning would also remove a small amount of the carbon each time, which would require that the resonator (or just its electrodes) be replaced periodically. The UV-ozone does not remove any of the gold electrodes, therefore gold electrodes are preferred.

One way to make a selective gas sensor is as follows. Since the sticking coefficient of a gas molecule is a function of the surface onto which the molecule impinges, one can use multiple unsealed resonators, each with a different set of electrode surfaces, to identify the gas molecules. For example, one set of electrodes can be gold, another copper, a third carbon (e.g. diamond), a fourth molybdenum, a fifth, sixth, etc. can be gold electrodes, each with a different UV-resistant polymer or enzyme coating, etc. The sensor would then be calibrated by exposing it to a variety of gases and recording the response of each resonator to each gas. From the variations of the responses to the variety of gases, one would develop a signature for each gas. The gases could be admitted to adsorb onto the clean resonator surfaces all at once, or the gas could be admitted in steps in order to determine the response of each resonator to adsorption after being partially contaminated.

An example of how this method would work is a laboratory or factory in which, say, six varieties of bottled toxic gases are used in a process. The sensor would be calibrated for each of the gases, then, when there is an accidental leak, the sensor would not only sound the alarm but also identify the particular gas that is leaking. The multiple resonators can be a set of discrete resonators, or a single quartz substrate with multiple sets of electrodes on it. Photolithographically produced multiple resonators on a single quartz plate could be one way to produce the multiple resonators.

An additional means of obtaining selectivity would take advantage of the fact that different adsorbents react differently to the desorbing action of UV-ozone. From the variations in frequency changes due to the desorbing actions of UV-ozone, one would develop additional signature information for each gas and thus be able to identify the contaminant gases. During calibration, one would first measure the frequency shift produced by adsorption of the gas, then the UV lamp would be turned on for short times, e.g., one second intervals, and the increases in frequencies due to the successive one second exposures would be recorded.

In addition to organic contamination, the atmosphere also contains airborne inorganic contaminants such as particles. Since particulate contamination usually cannot be removed by UV-ozone, allowing significant amounts of such contamination to accumulate on the sensor would be detrimental to the operation of the sensor.

Therefore, incorporation into the sensor apparatus of an air sampling pump and a particle filter (which filters the particles but not the organic contaminants) is desirable. Also desirable is the incorporation of means (e.g., via software) to compensate for the permanent frequency offsets caused by particles and other UV-ozone-resistant contaminants.

In FIG. 1 of the drawing, the ordinate represents the temperature compensated normalized frequency and the abscissa represents time. The point designated 10 is the frequency when no contamination is present on the electrodes. The point designated 12 on the ordinate represents the frequency change due to a monolayer of a light contaminant such as methane. The dashed line designated 14 represents, for example, 75 percent of a monolayer of contamination such as methane.

Point 14 is chosen during a calibration, for convenient interpretation of the results, such that for a constant contamination level, the $\Delta f/f$ vs. time is linear to a certain level, for example, to 5%. (As more and more contamination is adsorbed, the $\Delta f/f$ vs. time will become nonlinear because the sticking coefficient for a second layer of adsorbed contamination would, in general, be different from that of the first layer.)

In operation, when the detector is turned on, the UV-ozone lamps or cleaners are activated to clean the electrodes and are then shut off when frequency 10 is reached. The typical cleaning time might be a few seconds. As the contaminants from the atmosphere are adsorbed, the frequency decreases and the rate of frequency change with time is measured. That is, the slope at any point of the curve 10–16 is a measure of the atmospheric contaminant concentration at the particular time. When the point designated 16 is reached, the UV-ozone cleaners are automatically turned on until the frequency reaches the point designated 18. Then, the process continues. It is seen at the point designated 20, for example, that the concentration of contamination has suddenly increased When the invention is used as a toxic gas detector, the sudden increase in slope can trigger an alarm.

The desorption of contaminants could be aided by using a radiant heater in addition to the UV lamp.

The detector described would be superior to other detectors, because it is real-time, highly sensitive, simple-to-use, with no moving parts (and no wear), and it can be tailored to be either selective or nonselective by using appropriate adsorbers for electrodes.

Among the obvious applications of this detector are the detection of toxic gases, and the monitoring of contamination levels in clean rooms and other facilities where organic contamination can degrade device performance or manufacturing yields.

I wish it to be understood that I do not desire to be limited to the exact details of construction shown and described for obvious modifications will occur to a person skilled in the art.

What is claimed is:

1. A continuous method of sensing contamination in the atmosphere in which the rate of change of frequency of an unsealed dual mode quartz crystal resonator is used to measure the rate of change of contamination induced by the adsorption of contaminant molecules, said method including the steps of:
   (A) cleaning the electrodes of the resonator,
   (B) allowing contamination from the atmosphere to be adsorbed onto the resonator and simultaneously measuring the rate of change of frequency to measure the rate of change of contamination until nearly a monolayer compensating for temperature induced frequency shifts, and
   (C) repeating steps (A) and (B).

2. Method according to claim 1 where steps (A) and (B) are continuously repeated until it is no longer desired to sense the contamination in the atmosphere.

3. Method according to claim 1 wherein step (B) is carried out until 75 percent of a monolayer of contamination is adsorbed onto the resonator.

4. Method according to claim 1 wherein the electrodes are cleaned by the use of UV-ozone.

5. Method according to claim 1 wherein the method is used to sense toxic gas in the atmosphere.

6. Method according to claim 1 wherein the unsealed dual mode resonator is a 10 megahertz third overtone SC-cut resonator.

7. Method according to claim 1 wherein the electrodes are gold.

8. Method according to claim 1 wherein the electrodes are carbon.

9. Method according to claim 1 wherein the electrodes are selective for a particular contaminant.

10. A continuous method of sensing contamination in the atmosphere in which the rate of changes of frequency of multiple unsealed dual mode quartz crystal resonators, each with a different set of electrode surfaces, are used to measure the rate of change of contamination induced by the adsorption of contaminant molecules, said method including the steps of:
    (A) cleaning the electrodes of the resonators,
    (B) allowing contamination from the atmosphere to be adsorbed onto the resonators and simultaneously measuring the rate of change of frequency to measure the rate of change of contamination until nearly a monolayer of contamination has been adsorbed onto the resonators while compensating for temperature induced frequency shifts, and
    (C) repeating steps (A) and (B).

11. Method according to claim 10 wherein the multiple unsealed resonators are a set of discrete resonators.

12. Method according to claim 10 wherein the multiple unsealed resonators are a single quartz substrate with multiple sets of electrodes on it.

13. Method according to claim 10 wherein the variations in frequency changes due to the desorbing-actions of UV-ozone are used to identify the contaminant gases.

14. Method according to claim 10 wherein a particle filter is included to filter out UV-ozone resistant contaminants.

* * * * *